United States Patent
Nelson et al.

(10) Patent No.: US 8,058,479 B2
(45) Date of Patent: Nov. 15, 2011

(54) METHOD FOR PURIFYING ACETONE

(75) Inventors: Mark Erik Nelson, Mount Vernon, IN (US); Andrey Yurievich Sokolov, St. Petersburg (RU); Ilya Yurievich Krupenko, St. Petersburg (RU); Valery Yurievich Aristovich, St. Petersburg (RU)

(73) Assignee: Sabic Innovation Plastics IP B.V., Bergen Op Zoom (NL)

( * ) Notice: Subject to any disclaimer, the term of this patent is extended or adjusted under 35 U.S.C. 154(b) by 0 days.

(21) Appl. No.: 12/633,737

(22) Filed: Dec. 8, 2009

(65) Prior Publication Data

US 2010/0145103 A1 Jun. 10, 2010

(30) Foreign Application Priority Data

Dec. 9, 2008 (RU) .............................. 2008148187

(51) Int. Cl.
*C07C 45/78* (2006.01)
(52) U.S. Cl. ........................................ 568/411; 568/341
(58) Field of Classification Search .................. 568/341, 568/411
See application file for complete search history.

(56) References Cited

U.S. PATENT DOCUMENTS

| | | | |
|---|---|---|---|
| 3,215,745 | A | 11/1965 | Frank |
| 4,340,447 | A | 7/1982 | Laverick et al. |
| 4,722,769 | A | 2/1988 | Chan et al. |
| 6,340,777 | B1 | 1/2002 | Aristovich et al. |

FOREIGN PATENT DOCUMENTS

| | | |
|---|---|---|
| CA | 1016100 | 8/1977 |
| CA | 1016100 A1 | 8/1977 |

OTHER PUBLICATIONS

PCT International Search Report for International Application No. PCT/US2009/067293.
PCT Written Opinion of the International Searching Authority for International Application No. PCT/US2009/067293.

*Primary Examiner* — Sikarl Witherspoon
(74) *Attorney, Agent, or Firm* — Paul A. Jenny; Todd S. Hofmeister; Michael Best & Friedrich LLP

(57) ABSTRACT

A method for purifying a crude acetone raw material containing low molecular weight impurities using three columns in sequence is disclosed. The method comprises the steps of feeding the crude acetone raw material into a first column; adding an alkaline reagent and an oxidative reagent into the first column; feeding the first bottom fraction to a second rectification column; optionally adding an alkaline reagent to the second column above the charge point of the bottom fraction; separating a purified acetone from the high molecular weight impurities and removing the purified acetone as a top fraction by distillation in the second column, thereby forming a second bottom fraction comprising an acetone mixture comprising high molecular weight impurities; feeding the second bottom fraction comprising the acetone mixture to a third rectification column; removing a top fraction from the third column; and returning the top fraction removed from the third column to the first column, wherein the second rectification column is operated at atmospheric pressure, and wherein the purified acetone has an acetaldehyde level of less than 5 ppm and a KT-Test time of greater than 11 hours, as measured by the SABIC KT-Test method.

20 Claims, 1 Drawing Sheet

FIGURE
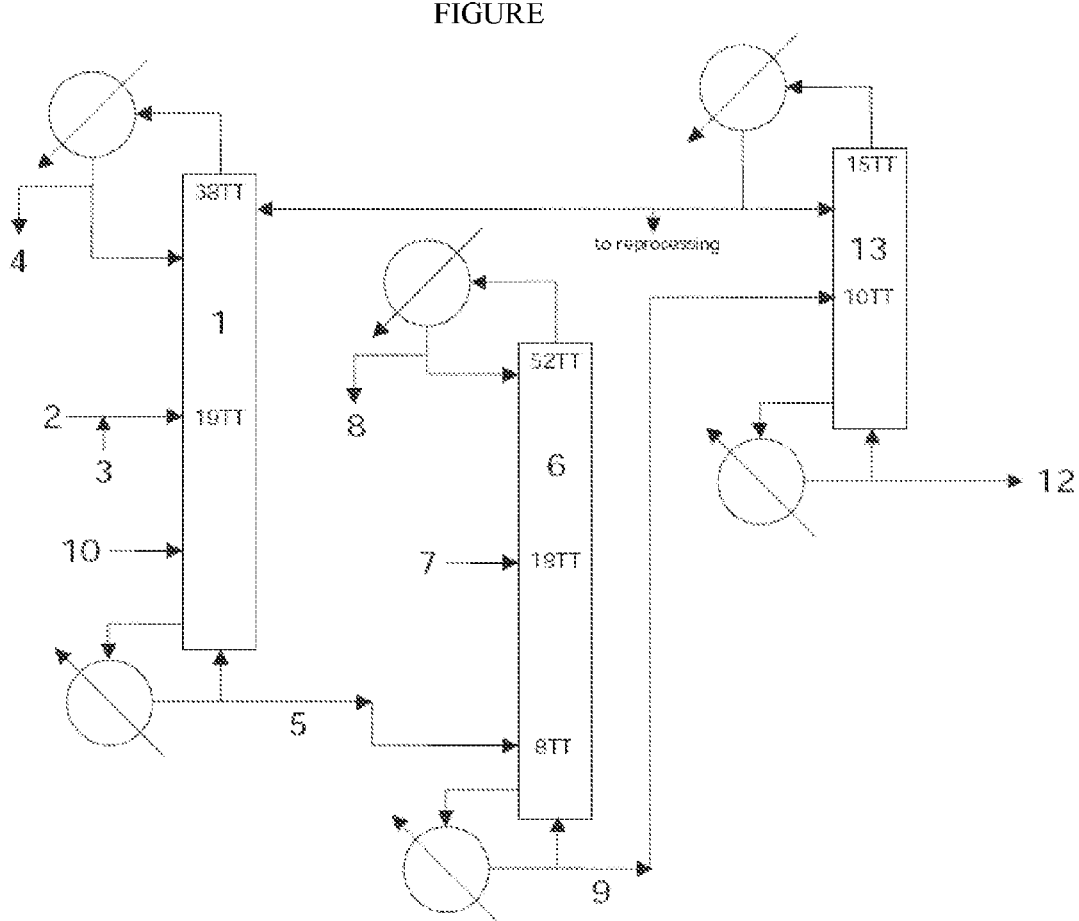

METHOD FOR PURIFYING ACETONE

CROSS REFERENCE TO RELATED APPLICATIONS

This application claims priority to Russian Application Serial No. 2008148187, filed Dec. 9, 2008. This disclosure is hereby fully incorporated herein by reference. This disclosure is hereby fully incorporated herein by reference. This application is related to Ser. No. 12/633,746 entitled "METHOD FOR PURIFYING ACETONE" and filed on Dec. 8, 2009. This related application is hereby incorporated by reference in its entirety

BACKGROUND

The present invention relates to the field of chemistry and, specifically, to the technology of organic synthesis; namely to the production of acetone obtained together with phenol during the decomposition of cumene hydroperoxide.

In addition to the basic products, which are acetone and phenol, an entire series of impurities having an adverse effect on the quality of the end product forms during the oxidation of cumene and subsequent decomposition of cumene hydroperoxide. After neutralization, acetone and phenol, the decomposition products of cumene hydroperoxide are fed to a fractionation column, in which they are separated into acetone raw material and phenol raw material fractions. Then, depending on the purification system used, the acetone raw material and phenol raw material fractions enter the appropriate stages of isolation and purification.

A method is known for purifying acetone raw material comprising subjecting the decomposition product to purification in two rectification columns wherein the acetone treated in the first rectification column is sent to the second rectification column, and purified acetone is discharged from the top of the second rectification column as a commercial product (see U.S. Pat. No. 3,215,745).

It is known, however, that use of simple distillation methods alone to purify acetone raw material is not completely effective since impurities, specifically, aliphatic aldehydes, olefins and a whole series of other impurities, remain in the treated acetone product, reducing its purity and quality.

A number of chemical treatment methods involving alkali metal hydroxides are known that are effective in causing low-boiling aldehydes to condense to high-boiling aldols that are then removed from the acetone by ordinary distillation (see, for example, U.S. Pat. Nos. 4,722,769 and 4,340,447). These references each disclose different processes for purifying acetone in the presence of an alkaline agent. The aldol derivatives formed are thermally unstable and decompose in the reboiler of the distillation column, thus producing low-boiling aldehydes. Both methods produce product (commercial) acetone having KT-Test values that are lower than desired.

A method for purifying acetone in which distillation of acetone raw material is carried out in three rectification columns in sequence is also known (see, for example, Canadian Patent No. 1016100). In this process, the second column is operated under reduced pressure, which increases operating costs and decreases operating capacity.

There is a need to provide a simple and flexible method for further purifying acetone (to reduce the levels of impurities) without regard to the quality of the acetone raw material.

SUMMARY OF THE INVENTION

The inventors have found that it is possible to produce high-quality acetone with maximum utilization of equipment and reagents and minimal capital expenditures for modernization. Some or all of the above-described deficiencies are addressed by a method for purifying a crude acetone raw material containing low molecular weight impurities, using three columns in sequence comprising the steps of: a) feeding the crude acetone raw material into a first column; b) adding an alkaline reagent and an oxidative reagent into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an alkaline reagent to the second column above the charge point of the bottom fraction fed in step d); f) separating a purified acetone from the high molecular weight impurities and removing the purified acetone as a top fraction by distillation in the second column, thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11 hours, as measured by the SABIC KT-Test method.

In another embodiment, a method for purifying a crude acetone raw material containing low molecular weight impurities, using three columns in sequence comprises the steps of: a) feeding the crude acetone raw material into a first column; b) adding an aqueous sodium hydroxide solution and an aqueous oxidative reagent solution into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an aqueous oxidative reagent solution to the second column above the charge point of the bottom fraction fed in step d); f) separating a purified acetone from the high molecular weight impurities and removing the purified acetone as a top fraction by distillation in the second column, thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11 hours, as measured by the SABIC KT-Test method.

In yet another embodiment, a method for purifying a crude acetone raw material containing low molecular weight impurities, using three columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an aqueous sodium hydroxide solution to the second column above the charge point of the bottom fraction fed in step d); f) separating a purified acetone from the high molecular weight impurities and removing the purified acetone as a top fraction by distillation in the second column; thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, wherein the weight ratios of the sodium hydroxide solution to the aqueous oxidative reagent solution are between 1:0.5 to 1:10, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

It has been discovered that it is possible to produce commercial (purified) acetone with a KT-Test time of at least 11.0 hours, specifically at least 12.0 hours, and an acetaldehyde level of less than 5 ppm, specifically less than 4 ppm, as measured by gas chromatography from a calibration curve obtained using acetaldehyde/acetone standards, and when operating the columns at optimum conditions. Both an alkaline and an oxidative reagent must be added in order for the method to achieve the desired results, but minimal capital expenditures for modernization of existing equipment are needed, making this method desirable. In some embodiments, an alkaline reagent is added to both the first and the second column. The addition of the oxidative reagent to the first column is a benefit for systems running under both vacuum and those at atmospheric pressure. Additionally, use of the oxidative reagent makes the process more reliable than a similar process without the oxidative reagent.

The top fraction (distillate) of the third rectification column is recycled into the first column charge or at a point in the first rectification column, desirably in the top part of the first column or in any other preceding flow for subsequent reprocessing.

BRIEF DESCRIPTION OF THE DRAWING

The FIGURE is a process flow diagram of the three column rectification process of the invention.

DETAILED DESCRIPTION OF THE INVENTION

The inventors have found a way to further reduce the amount of impurities in acetone by a method for purifying a crude acetone raw material containing low molecular weight impurities, using three columns in sequence comprising the steps of: a) feeding the crude acetone raw material into a first column; b) adding an alkaline reagent and an oxidative reagent into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an alkaline reagent to the second column above the charge point of the bottom fraction fed in step d); f) separating a purified acetone from the high molecular weight impurities and removing the purified acetone as a top fraction by distillation in the second column, thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

In embodiments, the alkaline reagent is an organic or an inorganic base. In an embodiment, the alkaline reagent is an aqueous alkaline solution, specifically an aqueous alkaline solution having an alkali salt concentrations of from 0.1 wt % to 30 wt %, more specifically sodium hydroxide. In an embodiment, the alkaline reagent is fed to the first rectification column in amount of from 0.05 wt % to 0.8 wt % of the crude acetone raw material fed to the first column, and the alkaline reagent is fed to the second rectification column in an amount of from 0.03% to 0.5% of the crude acetone raw material fed to the first column.

In an embodiment, the oxidative reagent is an organic or an inorganic oxidative reagent or a combination of one or more organic or inorganic reagents. In an embodiment, the oxidative reagent is selected from the group consisting of hydrogen peroxide, methylhydroperoxide, cumene hydroperoxide and potassium permanganate, specifically hydrogen peroxide and potassium permanganate. In an embodiment, the oxidative reagent is an aqueous solution comprising from 0.1 wt % to 30 wt % oxidative reagent. In another embodiment, the oxidative reagent solution is fed to the first rectification column in an amount of from 0.02 wt % to 0.50 wt % of the crude acetone raw material charge. In an embodiment, the oxidative reagent is an aqueous solution comprising from 0.1 wt % to 30 wt % oxidative reagent and the oxidative reagent solution is fed to the first rectification column in an amount of from 0.02 wt % to 0.50 wt % of the crude acetone raw material charge.

In an embodiment, the purified acetone has an acetaldehyde level of less than 4 ppm as measured by gas chromatography from a calibration curve obtained using acetaldehyde/ acetone standards. In another embodiment, the purified acetone has KT-Test time of greater than or equal to 12.0 hours, as measured by the SABIC KT-Test method.

In another embodiment, a method for purifying a crude acetone raw material containing low molecular weight impurities, using three columns in sequence comprises the steps of: a) feeding the crude acetone raw material into a first column; b) adding an aqueous sodium hydroxide solution and an aqueous oxidative reagent solution into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an aqueous oxidative reagent solution to the second column above the charge point of the bottom fraction fed in step d); f) separating a purified acetone from the high molecular weight impurities and removing the purified acetone as a top fraction by distillation in the second column, thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

In yet another embodiment, a method for purifying a crude acetone raw material containing low molecular weight impurities, using three columns in sequence comprises the steps of: a) feeding the crude acetone raw material into a first column; b) adding an aqueous sodium hydroxide solution and an aqueous hydrogen peroxide solution into the first column to form high molecular weight impurities; c) removing a top fraction from the first column by distillation to form a first bottom fraction comprising an acetone mixture comprising high molecular weight impurities; d) feeding the first bottom fraction comprising the acetone mixture obtained in step c) to a second rectification column at a charge point on the column; e) optionally adding an aqueous sodium hydroxide solution to the second column above the charge point of the bottom fraction fed in step d); f) separating a purified acetone from the high molecular weight impurities and removing the purified acetone as a top fraction by distillation in the second column; thereby forming a second bottom fraction comprising an acetone mixture comprising high molecular weight impurities; g) feeding the second bottom fraction comprising the acetone mixture obtained in step f) to a third rectification column at a charge point on the column; h) removing a top fraction from the third column by distillation to form a third bottom fraction comprising high molecular weight impurities; and i) returning the top fraction removed from the third column to the first column; wherein the second rectification column is operated at atmospheric pressure, wherein the weight ratios of the sodium hydroxide solution to the aqueous oxidative reagent solution are between 1:0.5 to 1:10, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

In an embodiment, the purified acetone has an acetaldehyde level of less than 4 ppm as measured by gas chromatography from a calibration curve obtained using acetaldehyde/acetone standards and a KT-Test time of greater than 12 hours, as measured by the SABIC KT-Test method.

The method of the present invention is a reliable, economical and simple method for removing aldehydes and other unsaturated impurities from acetone raw material, wherein the alkaline and oxidative reagents are used in such quantities that the acetone itself is not subject to their harmful action during production of high quality, purified commercial grade acetone that does not contain aldehydes or contains very low levels of aldehydes. Use of the third column in combination with the oxidative reagent added to the first column improves acetone purity and yields over a two column system.

The first, second and third rectification columns are desirably operated at atmospheric pressure or at a pressure below atmospheric, specifically at atmospheric pressure.

In normal cumene hydroperoxide decomposition that produces acetone and phenol, the acetone raw material contains acetone, water, aldehydes, $\alpha,\beta$-unsaturated carbonyls, cumene and alpha-methyl-styrene. The acetone raw material to be purified (containing these impurities) is fed to an purification section of the plant consisting of three distillation columns for isolation and purification of the acetone. The majority of low-boiling (low molecular weight) acetone impurities, such as the various aldehydes, are removed from the first rectification column in the top fraction. An alkaline reagent is also fed to the first rectification column to convert the remaining portion of aldehydes and $\alpha,\beta$-unsaturated carbonyls into high-boiling (high molecular weight) components. The alkaline reagent may be fed into the first rectification column at any desirable point, such as into the raw material acetone charge, into the column bottoms and/or any other desired point to convert aldehydes to aldols. All the remaining components, including the acetone, are removed from the first rectification column as the bottom fraction and are fed to the second rectification column. Commercial (purified) acetone is recovered from the top of the second rectification column, while residual aldols, water, and other high-boiling impurities (cumene, alpha-methyl-styrene) are removed from the second column as the bottom fraction and are fed to the third rectification column. In the third column, a top fraction is taken off the column, which removes the remaining acetone and low-boiling (low molecular weight) impurities formed as a result of the breakdown of aldols, and returns them back to the first column for reprocessing and separation (or other method for processing if desired). The heavy or high molecular weight impurities are removed as a bottom fraction and sent for subsequent processing or purification as desired. An alkaline reagent may also be fed to the second rectification column, if desired. In practice, some of the alkaline reagent is not used up and will remain in the bottoms, which are fed to the second column. Additional alkaline reagent may also be added if desired. The alkaline reagent is fed to the second rectification column at a point above the feed from the first rectification in order to remove any residual aldehydes by condensation to aldols.

An alkaline reagent is supplied to the first, and in some cases, to the second columns. It is desirable to add the alkaline reagent to the feed and/or to the bottom portion in the first column, and to a point above the feed supply tray in the second column. The alkaline reagent may be the same or different in the two columns.

If an alkaline reagent is used in both the first and second columns, the most efficient results are achieved when an optimum weight ratio of the alkaline reagent fed to the first rectification column and alkaline reagent fed to the second rectification column is from about 1:0.04 to 1:10, specifically from about 1:0.1 to 1:5. Operating at this ratio allows operation of the second column under atmospheric pressure, which significantly increases capacity compared to a second column operated under vacuum.

Any organic or inorganic base, specifically a base that is water soluble, may be used as the alkaline reagent. Specific examples of alkaline reagents include, but are not limited to, carbonates and hydroxides of alkaline metals, such as sodium hydroxide and potassium hydroxide, sodium phenate, and amines and polyamines (such as ethylenediamine and tetraethylenepentamine), specifically sodium hydroxide. The alkaline reagent may be an aqueous solution, and in some embodiments, at least about a 20% aqueous solution. Other aqueous solutions may be used but the amounts of water may affect the amounts used and the efficiency of the columns.

Since acetone raw material generally contains an increased quantity of unsaturated impurities such as, for example, unsaturated carbonyl-containing compounds and the like, an oxidative reagent is used for the more effective removal of these impurities during the distillation process. The oxidative reagent is added to the first column, preferably to the lower portion of the first column.

Organic or inorganic oxidizers and, specifically, organic or inorganic peroxides, may be used as the oxidative reagent. Examples of oxidative reagents include, but are not limited to, hydrogen peroxide, methylhydroperoxide, and cumene hydroperoxide and any other inorganic oxidizers such as potassium permanganate, sodium peroxide and sodium percarbonate, specifically hydrogen peroxide, methylhydroperoxide, cumene hydroperoxide and potassium permanganate, more specifically hydrogen peroxide and potassium permanganate. The oxidative reagent may be used in the form of an aqueous reagent at 0.1 to 30 wt %.

In chemical oxidation of this type, the low-boiling components and unsaturated carbonyl impurities are converted to their high-boiling derivatives (which are generally organic acids), which are soluble in water and resistant to thermal decomposition. These high-boiling derivatives along with the majority of the acetone are removed in the bottom fraction of the first column, which is then fed to the second column. The high-boiling derivatives, along with a small amount of acetone, are then removed from the second column as the bottom fraction and are fed to the third column. The high-boiling derivatives are then removed from the third column as the bottom fraction and may be sent for further processing, separating or disposal. The top fraction from the third column, including the small amount of acetone that was discharged from the second column bottoms, is sent back to the top portion of the first column for reprocessing. Since a significant portion of the original impurities contained in the raw acetone material are converted to organic acids or other derivatives rather than aldols by addition of the oxidative reagent, there is less re-conversion to aldehydes. Use of both an oxidative reagent and a third column in the purification process make it possible to significantly reduce the temperature of the second column, where the purified (commercial) acetone is isolated, because of the incomplete isolation of acetone in it and the further removal of acetone in the third column. Reducing the temperature in the second column substantially reduces the breakdown of aldols into original aldehydes, which are of lower molecular weight and would rise to the top of the second column and contaminate the purified acetone distillate.

Optimum or most efficient removal of aldehydes and unsaturated impurities is best achieved when the selected ratio between the alkaline and oxidative reagents is used. Use of excess reagents may still remove the impurities, but this will result in an inefficient and/or less cost effective operation of the process.

The "KT-test" (permanganate test for time, an oxidation test using a solution of potassium permanganate) is widely used as an analytical test for determining the total quantity of aldehydes and other reducible impurities contained in commercial acetone. A large percentage of the acetone currently sold commercially on the market has a minimal KT-test value equal to about 2 hours. Using the method of the invention, it is possible to produce commercial (purified) acetone that has a KT-test time greater than 11.0, and specifically at least 12.0 hours.

Another quality indicator is the measured level of aldehyde, specifically acetaldehydes, in the commercial acetone, and a desirable level is less than 5 ppm, specifically less than 4. In some cases, there may be other important indicators of quality for commercial acetone, such as, for example, the water and diacetone alcohol content of the acetone.

Referring to the FIGURE, which is a process flow diagram of a three column rectification (or purification) process, the acetone raw material charge 2 is fed to the first rectification column 1, where the top fraction 4 or low-boiling acetone impurities, are isolated and removed from the first column. An alkaline reagent 3, such as sodium hydroxide, is also fed to the first column 1 to convert the residual aldehydes, $\alpha,\beta$-unsaturated carbonyl-containing compounds and other remaining impurities to high-boiling components. An oxidative reagent 10 (that is effective for oxidizing aldehydes to organic acids), such as hydrogen peroxide, is also fed to the first column 1. After removal of the top fraction 4 (also referred to as a low molecular weight purge), the remaining column contents 5 are fed to the second rectification column 6. In the second column 6, the acetone is cleansed of any residual aldols, water and other high-boiling impurities and is removed in the form of a distillate 8. An alkaline reagent 7 may also fed to the second rectification column 6, and if used, is fed above the charge tray to remove residual aldehydes and other impurities. It is desirable to maintain a specific weight ratio of alkaline reagent (such as sodium hydroxide) to oxidative reagent (such as hydrogen peroxide), such as from 1:0.1 to 1:100, and specifically from 1:0.5 to 1:10. If an alkaline reagent is fed to both the first and second columns, it is desirable to maintain a specific ratio of the alkaline reagent in the first rectification column to the alkaline reagent in the second rectification column, such as from 1:0.04 to 1:10.

A large percentage of the acetone is cleansed of residual aldols, water and other high-boiling impurities in the second column 6 and is collected as a distillate 8, while the remaining acetone, water, cumene, alpha-methylstyrene and other high-boiling components 9 are fed as the bottom fraction to the third rectification column 13 (also referred to as an acetone stripper column). The remaining acetone, aldehydes that form as a result of the breakdown of aldols, and other low-boiling impurities are removed as a top fraction 11 and are returned to the first column 1 (or alternatively, to any other point or stream that precedes the first column 1 for subsequent reprocessing. The bottom fraction 12 of the third rectification column 13 is sent for subsequent reprocessing or other handling as desired.

The method is illustrated by the following non-limiting examples.

EXAMPLES

The following test procedures were used to determine the KT-Test values and the amount of acetaldehyde in the acetone.

Permanganate Test Procedure (KT-Test) (also referred to as the "SABIC KT-Test")

A graduated glass cylinder (50 ml) was filled with a sample of commercial acetone to the 50 ml mark. A 2 ml sample of a 0.02 wt % aqueous solution of potassium permanganate was added to the acetone sample and the solutions mixed well. The cylinder containing the acetone/potassium mixture was placed in a water bath maintained at 25° C. The color of the acetone/potassium permanganate mixture was observed every 30 minutes for loss of the red-purple color. The KT-Test value was determined by the number of hours required for the acetone/permanganate solution to fade to the orange-pink color of a standard color solution (prepared by dissolving 0.280 grams of uranyl nitrate hexahydrate and 0.170 grams of cobaltous chloride hexahydrate in 50 ml of distilled water).

Acetaldehyde Test Procedure

A GC HP5890 gas chromatograph equipped with a dual FID detector and using a 1 m by 5 mm (outside diameter) glass column packed with Cromosorb 102 on 80/100 Supelcoport measured acetaldehyde content in commercial acetone samples. The gas chromatogram operating conditions included an oven temperature of 120° C., an injector temperature of 200° C., a detector temperature of 250° C. with an argon flow of 30 ml/min, a hydrogen flow of 30 ml/min and air flow of 300 ml/min. Total sample run time was 10 minutes. The acetaldehyde content in commercial acetone samples was determined from a calibration curve obtained by injecting 1.0 micro liter control samples of standard mixtures of acetaldehyde free acetone and freshly distilled acetaldehyde containing 5, 10, 20, 40, 70 and 100 ppm of acetaldehyde in acetaldehyde-free acetone.

Eight comparative examples and three comparative examples were run to illustrate the invention. The operating parameters and a summary of the results from the runs are shown in Tables 1 and 2 below.

Comparative Example 1

(CEx.1)

Three Columns, No Oxidative Reagent, Alkaline Reagent in Columns 1 and 2

Crude acetone obtained from the process of producing phenol from cumene containing up to 65 wt % of acetone and a corresponding quantity of water, cumene and alpha-methyl styrene was fed to a three column laboratory purification system (as detailed in the FIGURE) for isolation and purification of acetone. The acetone also contained traces (at the level of ppm) of such compounds as acetaldehyde, propionaldehyde, methanol, mesityl oxide and other unsaturated carbonyls, as well as diacetone alcohol and phenol.

The crude acetone (raw material) 2 at a temperature of 50° C. was fed to the first rectification column 1, which was filled with Levin packing and had an efficiency of 38 theoretical trays (TT) and a temperature of 50° C. The acetone charge was fed at theoretical tray 19 (as counted starting from the bottom of the column). A 20% sodium hydroxide (NaOH) aqueous solution 3 was fed into the column charge in an amount of 0.50 wt % of the column charge. The column operated at atmospheric pressure. While a temperature of 55 to 56° C. was maintained at the top of the column, and a reflux ratio of 50, the top fraction 4 was taken off in an amount of 1.5 to 2.0 wt % of the charge. The top fraction 4 contained a large percentage of low-boiling impurities including acetaldehyde. The temperature of the column reboiler was 67 to 68° C. The bottoms 5 of the first column was fed to the second rectification column 6 for subsequent processing in an amount of 98 to 98.5 wt % of the charge. The bottoms fraction contained acetone, cumene, alpha-methylstyrene, water and other impurities, including the products of aldol condensation.

The second rectification column 6 was also filled with Levin packing having an efficiency of 51.8 TT. The column operated at atmospheric pressure. The bottoms 5 were fed at theoretical tray 8 (counting from the bottom of the column). Purified commercial grade acetone was collected from the top of the column in the form of a vapor and was completely condensed, and the liquid portion was taken in batches as the end product 8, while the reflux was returned to the top of the column 6. The temperature at the top of the second column was kept at about 56° C. The two-phase bottoms product 9 from the second column 6 contained water, cumene and alpha-methylstyrene, traces of carbonyls, products of aldol condensation, phenol, phenolate and NaOH residues. The bottoms product 9 was fed to the third rectification column 13 for further processing. The temperature of the second column reboiler was kept at an average of about 82.1° C., and the reflux number was about 2.2

The third rectification column 13 was also filled with Levin packing having an efficiency of 15 TT. The column was operated at atmospheric pressure. The bottoms 9 were fed at theoretical tray 10. The remaining acetone and other low-boiling impurities, such as acetaldehyde, were removed as the top fraction 11. The temperature at the top of the third column 13 was of 55 to 60° C. The temperature of the column reboiler was at least 100° C. to isolate the remaining acetone, and the reflux number was about 25. The bottom fraction 12 of the third column contained cumene, alpha-methylstyrene, water and other impurities, including the products of aldol condensation, phenol and sodium hydroxide collected from the column and was sent for further processing as desired.

Sodium hydroxide (NaOH) (20 wt % aqueous solution) 7 is also fed to the second column at theoretical tray 18 (counting from the bottom) in an amount of 0.10 wt % of the first column charge 2.

Comparative Example 2

(CEx.2)

Three Columns, No Oxidative Reagent, Alkaline Reagent in Columns 1 and 2

Crude acetone raw material obtained from the cumene process was again purified. In Comparative Example 2, the NaOH (20 wt % aqueous solution) charge 7 was supplied to the second rectification column 6 at theoretical tray 18 in an amount of 0.10 wt % of the first column charge 2. The reflux number of the second column was kept at an average of about 2.3, and the temperature of the second column was kept at an average of about 83.3° C. The reflux number of the third column was kept at an average of about 20. All other conditions were the same as in Comparative Example 1.

Comparative Example 3

(CEx.3)

Three Columns, No Oxidative Reagent, Alkaline Reagent in Columns 1 and 2

Crude acetone raw material from the cumene process was again purified. In Comparative Example 3, the NaOH (20 wt % aqueous solution) 7 was supplied at theoretical tray 18 of the second column 6 in an amount of 0.10 wt % of the charge 2. The reflux number in the second column is kept at an average of about 2.2, and the temperature of the second column was kept at an average of about 85.4° C. The reflux number of the third column was kept at an average of about 30. All other conditions were the same as in Comparative Example 1.

Example 1

(Ex.1)

Three Columns, Oxidative Reagent, Alkaline Reagent in Column 1 Only

Acetone raw material from the cumene process was again purified. In Example 1, the NaOH (20 wt % aqueous solution) charge 3 was fed to the first column 1 in an amount of 0.10 wt % of the charge in the first column. In addition, a 5 wt % aqueous solution of hydrogen peroxide 10 was fed to the column in an amount of 0.20 wt % of the charge 2 to the column 1. No NaOH (20 wt % aqueous solution) was supplied to the second column. The reflux number of the second column was kept at an average of about 2.1, and the temperature of the second column was kept at an average of about 80.1° C. The reflux number of the third column was kept at an average of about 15. All other conditions were the same as in Comparative Example 1.

Example 2

(Ex.2)

Three Columns, Oxidative Reagent, Alkaline Reagent in Column 1 Only

Acetone raw material from the cumene process was again purified. In Example 2, the NaOH (20 wt % aqueous solution) charge 3 was fed to the first column 1 in an amount of 0.10 wt % of the charge in the first column. In addition, a 5 wt % aqueous solution of hydrogen peroxide 10 was fed to the column in an amount of 0.20 wt % of the charge 2 to the column 1. No NaOH (20 wt % aqueous solution) was supplied to the second column. The reflux number of the second column was kept at an average of about 2.3, and the temperature of the second column was kept at an average of about 84.6° C. The reflux number of the third column was kept at an average of about 25. All other conditions were the same as in Comparative Example 1.

Example 3

(Ex.3)

Three Columns, Oxidative Reagent, Alkaline Reagent in Columns 1 and 2

Acetone raw material from the cumene process was again purified. In Example 3, the NaOH (20 wt % aqueous solution) charge 3 was fed to the first column 1 in an amount of 0.20 wt % of the charge in the first column. In addition, a 1 wt % aqueous solution of potassium permanganate (instead of hydrogen peroxide) 10 was fed to the column in an amount of 0.50 wt % of the charge 2 to the column 1. NaOH (20 wt % aqueous solution) 7 was supplied at theoretical tray 20 of the second column 6 in an amount of 0.03 wt % of the charge 2. The reflux number of the second column was kept at an average of about 2.1, and the temperature of the second column was kept at an average of about 85.1° C. The reflux number of the third column was kept at an average of about 25. All other conditions were the same as in Comparative Example 1.

Comparative Example 4

(CEx.4)

Three Columns, No Oxidative Reagent, Alkaline Reagent in Column 1 Only

Acetone raw material from the cumene process was again purified. In Comparative Example 4, the NaOH (20 wt % aqueous solution) charge 3 was fed to the first column 1 in an amount of 0.50 wt % of the charge in the first column. The reflux number of the second column was kept at an average of about 2.2, and the temperature of the second column was kept at an average of about 83.5° C. The reflux number of the third column was kept at an average of about 25. All other conditions were the same as in Comparative Example 1.

Comparative Example 5

(CEx.5)

Three Columns, No Oxidative Reagent, Alkaline Reagent in Column 1 Only

Acetone raw material from the cumene process was again purified. In Comparative Example 5, the NaOH (20 wt % aqueous solution) charge 3 was fed to the first column 1 in an amount of 0.50 wt % of the charge in the first column. The reflux number of the second column was kept at an average of about 2.2, and the temperature of the second column was kept at an average of about 79.7° C. The reflux number of the third column was kept at an average of about 25, the pressure in the bottom of the third column was kept at an average of about 900 mm Hg, and the temperature of the second column was kept at an average of about 60.5° C. All other conditions were the same as in Comparative Example 1.

Comparative Example 6

(CEx.6)

Two Columns, No Oxidative Reagent, Alkaline Reagent in Columns 1 and 2

Crude acetone obtained from the process of producing phenol from cumene containing up to 65 wt % of acetone and a corresponding quantity of water, cumene and alpha-methyl styrene was fed to a two column laboratory purification system (as detailed in the FIGURE) for isolation and purification of acetone. The acetone also contained traces (at the level of ppm) of such compounds as acetaldehyde, propionaldehyde, methanol, mesityl oxide and other unsaturated carbonyls, as well as diacetone alcohol and phenol.

The crude acetone (raw material) 2 at a temperature of 50° C. was fed to the first rectification column 1, which was filled with Levin packing and had an efficiency of 38 theoretical trays (TT). The acetone charge was fed at theoretical tray 19 (as counted starting from the bottom of the column). A 20% sodium hydroxide (NaOH) aqueous solution 3 was fed into the column charge in an amount of 0.50 wt % of the column charge. The column operated at atmospheric pressure. While a temperature of 55 to 56° C. was maintained at the top of the column, and a reflux ratio of 50, the top fraction 4 was taken off in an amount of 1.5 to 2.0 wt % of the charge. The top fraction 4 contained a large percentage of low-boiling impurities including acetaldehyde. The temperature of the column reboiler was 67 to 68° C. The bottoms 5 of the first column was fed to the second rectification column 6 for subsequent processing in an amount of 98 to 98.5 wt % of the charge. The bottoms fraction contained acetone, cumene, alpha-methylstyrene, water and other impurities, including the products of aldol condensation.

The second rectification column 6 was also filled with Levin packing having an efficiency of 51.8 TT. The column operated at atmospheric pressure. The bottoms 5 were fed at theoretical tray 8 (counting from the bottom of the column). Purified commercial grade acetone was collected from the top of the column in the form of a vapor and was completely condensed, and the liquid portion was taken in batches as the end product 8, while the reflux was returned to the top of the column 6. The temperature at the top of the second column was kept at about 56° C. The two-phase bottoms product 9 from the second column 6 contained water, cumene and alpha-methylstyrene, traces of carbonyls, products of aldol condensation, phenol, phenolate and NaOH residues. The bottoms product 9 was collected from the column and was sent for further processing as desired.

Sodium hydroxide (NaOH) (20 wt % aqueous solution) 7 is also fed to the second column at theoretical tray 18 (counting from the bottom) in an amount of 0.05 wt % of the first column charge 2. The reflux number of the second column was kept at an average of about 2.0. The temperature in the second column was maintained about 101.9° C.

Comparative Example 7

(CEx.7)

Two Columns, No Oxidative Reagent, Alkaline Reagent in Columns 1 and 2

Crude acetone raw material obtained from the cumene process was again purified. In Comparative Example 7, the NaOH (20 wt % aqueous solution) charge 7 was supplied to the second rectification column 6 at theoretical tray 18 in an amount of 0.10 wt % of the first column charge 2. The reflux number of the second column was kept at an average of about 2.0, and the temperature of the second column was kept at an average of about 101.5° C. All other conditions were the same as in Comparative Example 6.

Comparative Example 8

(CEx.8)

Two Columns, with Oxidative Reagent, Alkaline Reagent in Columns 1 and 2

Crude acetone raw material from the cumene process was again purified. In Comparative Example 8, the NaOH (20 wt % aqueous solution) charge 3 was fed to the first column 1 in an amount of 0.10 wt % of the charge in the first column. In addition, a 5 wt % aqueous solution of hydrogen peroxide 10 was fed to the column in an amount of 0.15 wt % of the charge 2 to the column 1. NaOH (20 wt % aqueous solution) 7 was supplied at theoretical tray 18 of the second column 6 in an amount of 0.05 wt % of the charge 2. The reflux number of the second column was kept at an average of about 2.0. All other conditions were the same as in Comparative Example 6.

TABLE 1

Basic technological parameters

| | First column | | | | | | Second column | | | | Third column | | | |
|---|---|---|---|---|---|---|---|---|---|---|---|---|---|---|
| | 20% aqueous solution NaOH | | 5% aqueous solution H$_2$O$_2$ | | Top fraction | | 20% aqueous solution NaOH | | | | Top fraction | | Temperature, °C | |
| Example | wt % of charge | Feed point | wt % of charge | Feed point | Reflux number | wt % of charge | wt % of first column charge | Feed point | Reflux number | Reboiler temp., °C | Reflux number | wt % of first column charge | Top | Bottom |
| CEx. 1 | 0.50 | Into Charge | — | — | 50 | 2.0 | 0.10 | TT 18 | 2.2 | 82.1 | 25 | 6.2 | 55.4 | 101.4 |
| CEx. 2 | 0.50 | Into Charge | — | — | 50 | 2.2 | 0.10 | TT 18 | 2.3 | 83.3 | 20 | 6.6 | 55.9 | 101.0 |
| CEx. 3 | 0.50 | Into Charge | — | — | 45 | 1.4 | 0.10 | TT 18 | 2.2 | 85.4 | 30 | 4.6 | 55.9 | 101.7 |
| CEx. 4 | 0.50 | Into Charge | — | — | 50 | 2.0 | — | — | 2.2 | 83.5 | 25 | 6.5 | 56.1 | 101.7 |
| CEx. 5 | 0.50 | Into Charge | — | — | 50 | 2.1 | — | — | 2.2 | 79.7 | 25 | 6.3 | 60.5 | 106.1 |
| CEx. 6 | 0.50 | Into Charge | — | — | 50 | 2.0 | 0.05 | TT 18 | 2.0 | 101.9 | — | — | — | — |
| CEx. 7 | 0.50 | Into Charge | — | — | 50 | 2.2 | 0.10 | TT 18 | 2.0 | 101.5 | — | — | — | — |
| CEx. 8 | 0.10 | Into Charge | 0.22 | Into Column | 50 | 1.8 | 0.05 | TT 18 | 2.0 | 102.5 | — | — | — | — |
| Ex. 1 | 0.10 | Into charge | 0.20 | Into Column | 45 | 1.5 | — | — | 2.1 | 80.1 | 15 | 7.0 | 55.8 | 101.2 |
| Ex. 2 | 0.10 | Into Charge | 0.20 | Into Column | 50 | 1.8 | — | — | 2.2 | 84.6 | 25 | 5.0 | 57.0 | 101.4 |
| Ex. 3 | 0.20 | Into Charge | 0.50 (KMnO$_4$, 1%) | TT 10 | 50 | 1.9 | 0.03 | TT 20 | 2.1 | 85.1 | 25 | 4.9 | 56.0 | 101.9 |

TABLE 1-continued

Basic technological parameters

| | First column | | | | Second column | | | | Third column | | | |
|---|---|---|---|---|---|---|---|---|---|---|---|---|
| | 20% aqueous solution NaOH | 5% aqueous solution H$_2$O$_2$ | Top fraction | | 20% aqueous solution NaOH | | Reboiler | | Top fraction | | Temperature, °C. | |
| Example | wt % of Feed charge / point | wt % of Feed charge / point | Reflux number | wt % of charge | wt % of first column Feed charge / point | Reflux number | temp., °C. | Reflux number | wt % of first column charge | Top | Bottom |

TABLE 2

Basic characteristics of purified (commercial) acetone

| | First column | Second column Commercial acetone | | | Third column | | |
|---|---|---|---|---|---|---|---|
| | Top fraction CH$_3$CHO, ppm | CH$_3$CHO, ppm | SABIC KT-Test, hours | Water, wt % (average value) | Top fraction CH$_3$CHO, ppm | Water, wt % (average value) | Bottom product Acetone in oil phase, wt. % |
| Example | | | | | | | |
| CEx. 1 | 682 | 6.0 | 27.0 | 0.13 | 1661 | 0.2 | traces |
| CEx. 2 | 452 | 1.9 | >48 | 0.05 | 1780 | 0.6 | traces |
| CEx. 3 | 677 | traces (<0.5) | >48 | 0.05 | 1922 | 0.4 | traces |
| CEx. 4 | 758 | 34.1 | 4.5 | 0.10 | 1916 | 0.5 | traces |
| CEx. 5 | 787 | 24.1 | 6.5 | 0.11 | 2538 | 0.6 | traces |
| CEx. 6 (2 columns) | 868 | 8.1 | 8.5 | 0.07 | — | — | — |
| CEx. 7 (2 columns) | 756 | 9.5 | 8.0 | 0.05 | — | — | — |
| CEx. 8 (2 columns) | 3224 | 4.5 | 10.5 | 0.05 | — | — | — |
| Ex. 1 | 4133 | 3.1 | 13.0 | 0.05 | 46 | 0.2 | traces |
| Ex. 2 | 3314 | 3.8 | 12.0 | 0.05 | 45 | 0.2 | traces |
| Ex. 3 | 2538 | 2.1 | >48 | 0.06 | 98 | 0.3 | traces |

As shown by the Examples, the combination of an alkaline reagent and an oxidative reagent in a three column purification process produces acetone at a very high purity level as shown by the KT-Test times and the amounts of residual acetaldehyde in the purified acetone. As shown by Comparative Example 5, when the third column is operated under a pressure above atmospheric pressure (for example, at 900 mm Hg), acetaldehyde content in top fraction is higher than if the third column operated at atmospheric pressure, as in the Examples. As shown by Comparative Examples 6 to 8, when only two columns are used, both the amount of acetaldehyde in the purified acetone and the KT-Test times are considerably worse than in the three column systems. Using an oxidative reagent in combination with an alkaline reagent results in a more stable and reliable process than one that uses only an alkaline reagent.

This method is a simple, economical method for producing high-quality (purified) commercial acetone that does not depend on the quality of the crude acetone raw material while also using the existing equipment. This will enable use of the method in chemical and other spheres of industry where removing impurities from the acetone is needed.

The singular forms "a," "an," and "the" include plural referents unless the context clearly dictates otherwise. Unless defined otherwise, technical and scientific terms used herein have the same meaning as is commonly understood by one of skill in the art to which this invention belongs. The modifier "about" used in connection with a quantity is inclusive of the stated value and has the meaning dictated by the context (e.g., includes the degree of error associated with measurement of the particular quantity). The terms "front", "back", "bottom", and/or "top" are used herein, unless otherwise noted, merely for convenience of description, and are not limited to any one position or spatial orientation. The endpoints of all ranges directed to the same component or property are inclusive and independently combinable (e.g., ranges of "less than or equal to about 25 wt %, or, more specifically, about 5 wt % to about 20 wt %," is inclusive of the endpoints and all intermediate values of the ranges of "about 5 wt % to about 25 wt %," etc.). The suffix "(s)" as used herein is intended to include both the singular and the plural of the term that it modifies, thereby including at least one of that term (e.g., the colorant(s) includes at least one colorants).

"Optional" or "optionally" means that the subsequently described event or circumstance can or cannot occur, and that the description includes instances where the event occurs and instances where it does not. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, –CHO is attached through carbon of the carbonyl group. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for purifying a crude acetone raw material containing low molecular weight impurities, using three columns in sequence comprising the steps of:
   a) feeding the crude acetone raw material into a first column;
   b) adding an alkaline reagent and an oxidative reagent into the first column to form high molecular weight impurities;
   c) removing a top fraction from the first column by distillation to form a first bottom fraction comprising an acetone mixture comprising high molecular weight impurities;
   d) feeding the first bottom fraction comprising the acetone mixture obtained in step c) to a second rectification column at a charge point on the column;
   e) optionally adding an alkaline reagent to the second column above the charge point of the bottom fraction fed in step d);
   f) separating a purified acetone from the high molecular weight impurities and removing the purified acetone as a top fraction by distillation in the second column, thereby forming a second bottom fraction comprising an acetone mixture comprising high molecular weight impurities;
   g) feeding the second bottom fraction comprising the acetone mixture obtained in step f) to a third rectification column at a charge point on the column;
   h) removing a top fraction from the third column by distillation to form a third bottom fraction comprising high molecular weight impurities; and
   i) returning the top fraction removed from the third column to the first column;
   wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

2. The method of claim 1 wherein the alkaline reagent is an organic or an inorganic base.

3. The method of claim 2 wherein the alkaline reagent is an aqueous alkaline solution.

4. The method of claim 3 wherein the aqueous alkaline solution is an aqueous alkaline solution having an alkali salt concentrations of from 0.1 wt % to 30 wt %, and wherein the alkaline reagent is fed to the first rectification column in amount of from 0.05 wt % to 0.8 wt % of the crude acetone raw material fed to the first column.

5. The method of claim 3 wherein the alkaline aqueous solution is sodium hydroxide.

6. The method of claim 1 wherein the oxidative reagent is an organic or an inorganic oxidative reagent or a combination of one or more organic or inorganic reagents.

7. The method of claim 6 wherein the oxidative reagent is selected from the group consisting of hydrogen peroxide, methylhydroperoxide, cumene hydroperoxide and potassium permanganate.

8. The method of claim 1 wherein the oxidative reagent is hydrogen peroxide or potassium permanganate.

9. The method of claim 1 wherein the oxidative reagent is an aqueous solution comprising from 0.1 wt % to 30 wt % oxidative reagent, and wherein the oxidative reagent solution is fed to the first rectification column in an amount of from 0.02 wt % to 0.50 wt % of the crude acetone raw material charge.

10. The method of claim 1 wherein the weight ratios of the alkaline reagent to the oxidative reagent are between 1:0.5 to 1:10.

11. The method of claim 1 wherein the weight ratios of the alkaline reagent in the first rectification column to the alkaline reagent in the second rectification column are between 1:0.1 to 1:5.

12. The method of claim 1 wherein the purified acetone has an acetaldehyde level of less than 4 ppm as measured by gas chromatography from a calibration curve obtained using acetaldehyde/acetone standards.

13. The method of claim 1 wherein the purified acetone has a KT-Test time of greater than 12 hours, as measured by the SABIC KT-Test method.

14. A method for purifying a crude acetone raw material containing low molecular weight impurities, using three columns in sequence comprising the steps of:
   a) feeding the crude acetone raw material into a first column;
   b) adding an aqueous sodium hydroxide solution and an aqueous oxidative reagent solution into the first column to form high molecular weight impurities;
   c) removing a top fraction from the first column by distillation to form a first bottom fraction comprising an acetone mixture comprising high molecular weight impurities;
   d) feeding the first bottom fraction comprising the acetone mixture obtained in step c) to a second rectification column at a charge point on the column;
   e) optionally adding an aqueous oxidative reagent solution to the second column above the charge point of the bottom fraction fed in step d);
   f) separating a purified acetone from the high molecular weight impurities and removing the purified acetone as a top fraction by distillation in the second column, thereby forming a second bottom fraction comprising an acetone mixture comprising high molecular weight impurities;
   g) feeding the second bottom fraction comprising the acetone mixture obtained in step f) to a third rectification column at a charge point on the column;
   h) removing a top fraction from the third column by distillation to form a third bottom fraction comprising high molecular weight impurities; and
   i) returning the top fraction removed from the third column to the first column;
   wherein the second rectification column is operated at atmospheric pressure, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

15. The method of claim 14 wherein the aqueous sodium hydroxide solution has an alkali salt concentrations of from 0.1 wt % to 30 wt %, and wherein the alkaline sodium hydroxide solution is fed to the first rectification column in amount of from 0.05 wt % to 0.8 wt % of the crude acetone raw material fed to the first column.

16. The method of claim 14 wherein the aqueous oxidative reagent solution is an aqueous solution comprising from 0.1 wt % to 30 wt % aqueous oxidative reagent, and wherein the aqueous oxidative reagent solution is fed to the first rectification column in an amount of from 0.02 wt % to 0.50 wt % of the crude acetone raw material charge.

17. The method of claim 14 wherein the weight ratios of the sodium hydroxide solution to the aqueous oxidative reagent solution are between 1:0.5 to 1:10.

18. The method of claim 14 wherein the aqueous oxidative reagent is selected from the group consisting of hydrogen peroxide, methylhydroperoxide, cumene hydroperoxide and potassium permanganate.

19. The method of claim 14 wherein the purified acetone has an acetaldehyde level of less than 4 ppm as measured by gas chromatography from a calibration curve obtained using acetaldehyde/acetone standards and a KT-Test time of greater than 12 hours, as measured by the SABIC KT-Test method.

20. A method for purifying a crude acetone raw material containing low molecular weight impurities, using three columns in sequence comprising the steps of:
 a) feeding the crude acetone raw material into a first column;
 b) adding an aqueous sodium hydroxide solution and an aqueous hydrogen peroxide solution into the first column to form high molecular weight impurities;
 c) removing a top fraction from the first column by distillation to form a first bottom fraction comprising an acetone mixture comprising high molecular weight impurities;
 d) feeding the first bottom fraction comprising the acetone mixture obtained in step c) to a second rectification column at a charge point on the column;
 e) optionally adding an aqueous sodium hydroxide solution to the second column above the charge point of the bottom fraction fed in step d);
 f) separating a purified acetone from the high molecular weight impurities and removing the purified acetone as a top fraction by distillation in the second column; thereby forming a second bottom fraction comprising an acetone mixture comprising high molecular weight impurities;
 g) feeding the second bottom fraction comprising the acetone mixture obtained in step f) to a third rectification column at a charge point on the column;
 h) removing a top fraction from the third column by distillation to form a third bottom fraction comprising high molecular weight impurities; and
 i) returning the top fraction removed from the third column to the first column;
 wherein the second rectification column is operated at atmospheric pressure, wherein the weight ratios of the sodium hydroxide solution to the aqueous oxidative reagent solution are between 1:0.5 to 1:10, and wherein the purified acetone has an acetaldehyde level of less than 5 ppm as measured by gas chromatography from a calibration curve obtained using acetaldehyde/acetone standards and a KT-Test time of greater than 11.0 hours, as measured by the SABIC KT-Test method.

* * * * *